US008886293B2

(12) United States Patent
O'Connor et al.

(10) Patent No.: US 8,886,293 B2
(45) Date of Patent: Nov. 11, 2014

(54) SYSTEM AND METHOD FOR TUMOR ANALYSIS AND REAL-TIME BIOPSY GUIDANCE

(75) Inventors: Michael K O'Connor, Rochester, MN (US); Carrie B Hruska, Mantorville, MN (US); Amanda L Weinmann, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/303,106

(22) Filed: Nov. 22, 2011

(65) Prior Publication Data

US 2012/0130234 A1 May 24, 2012

Related U.S. Application Data

(60) Provisional application No. 61/417,139, filed on Nov. 24, 2010.

(51) Int. Cl.
| | |
|---|---|
| *A61B 6/00* | (2006.01) |
| *A61B 6/04* | (2006.01) |
| *A61B 6/06* | (2006.01) |
| *A61B 6/12* | (2006.01) |
| *A61B 8/00* | (2006.01) |
| *A61B 8/08* | (2006.01) |
| *A61B 10/02* | (2006.01) |
| *A61B 10/00* | (2006.01) |

(52) U.S. Cl.
CPC ............... *A61B 6/0414* (2013.01); *A61B 6/06* (2013.01); *A61B 6/12* (2013.01); *A61B 6/4258* (2013.01); *A61B 6/4291* (2013.01); *A61B 6/48* (2013.01); *A61B 6/502* (2013.01); *A61B 8/403* (2013.01); *A61B 8/4209* (2013.01); *A61B 8/5261* (2013.01); *A61B 10/0233* (2013.01); *A61B 8/485* (2013.01); *A61B 10/0041* (2013.01)
USPC .......................................... 600/436; 600/407

(58) Field of Classification Search
CPC ......... G01T 1/29; G01T 1/161; G01T 1/1612; G01T 1/1617; G01T 1/164; G21K 1/02; G21K 1/025; G21K 1/001
USPC .................................. 600/407, 425, 427, 436
See application file for complete search history.

(56) References Cited

U.S. PATENT DOCUMENTS

| | | | |
|---|---|---|---|
| 3,777,148 A | 12/1973 | Miraldi | |
| 4,079,259 A | 3/1978 | Blum | |

(Continued)

FOREIGN PATENT DOCUMENTS

| | | |
|---|---|---|
| WO | 2010077626 A1 | 7/2010 |
| WO | 2010120525 A1 | 10/2010 |

OTHER PUBLICATIONS

"Quantification of lesion size, depth, and uptake using a dual-head molecular breast imaging system" by C.B. Hruska et al. Med. Phys. 35 (4). pp. 1365-1376. 2008.*

*Primary Examiner* — Tse Chen
*Assistant Examiner* — Jason Ip
(74) *Attorney, Agent, or Firm* — Yakov Sidorin; Quarles & Brady LLP

(57) ABSTRACT

A system and method for molecular breast imaging (MBI) provides enhanced tumor analysis and, optionally, a real-time biopsy guidance. The system includes a detector head including a gamma ray detector and a collimator. The collimator include multiple collimation sections having respectively different spatially-oriented structures. In addition or alternatively, the multiple collimating section have respectively different collimation characteristics. An image of the tissue acquired with the system may include spatially separate image portions containing image information about the same portion of the imaged tissue. A system is optionally configured to acquire updatable images to provide real-time feedback about the biopsy procedure.

14 Claims, 9 Drawing Sheets

(56) References Cited

U.S. PATENT DOCUMENTS

| | | |
|---|---|---|
| 4,181,839 A | 1/1980 | Hatton et al. |
| 4,419,585 A | 12/1983 | Strauss et al. |
| 4,597,096 A * | 6/1986 | Larsson ................. 378/149 |
| 4,792,686 A | 12/1988 | Karcher et al. |
| 6,353,227 B1 * | 3/2002 | Boxen ................. 250/363.1 |
| 6,424,693 B1 | 7/2002 | Weisenberger |
| 7,230,246 B2 | 6/2007 | Hawman |
| 2008/0249415 A1 * | 10/2008 | Okamura et al. ............ 600/445 |
| 2010/0016865 A1 | 1/2010 | Kieper et al. |

* cited by examiner

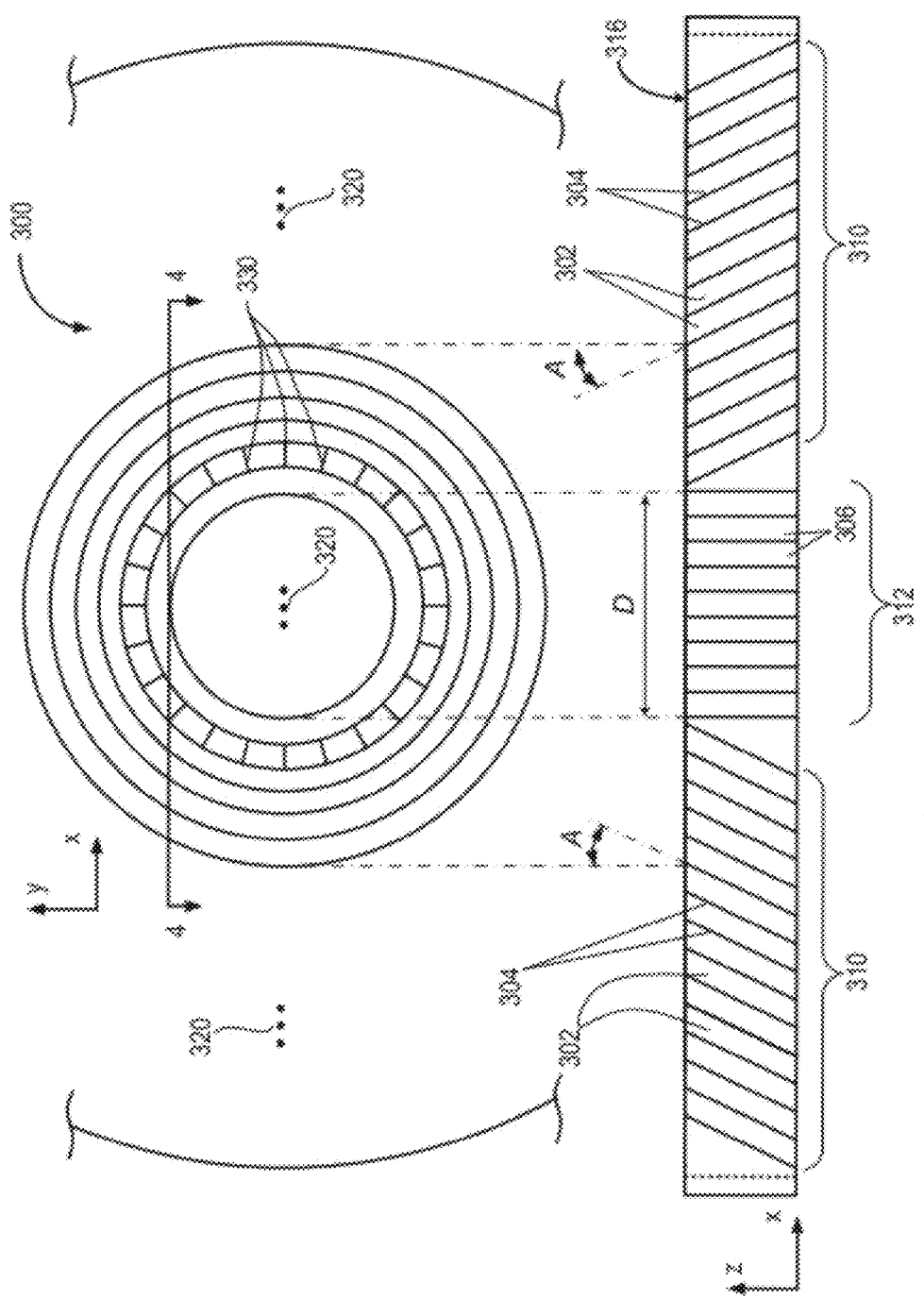

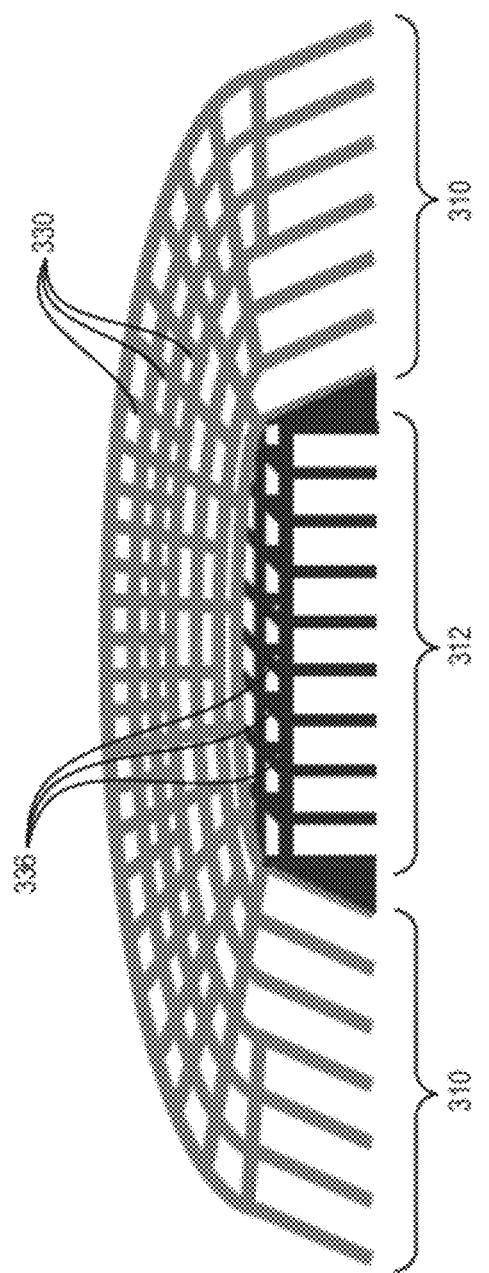

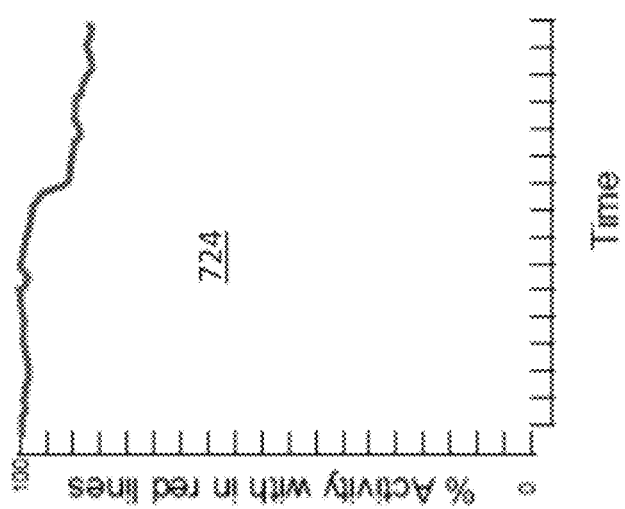
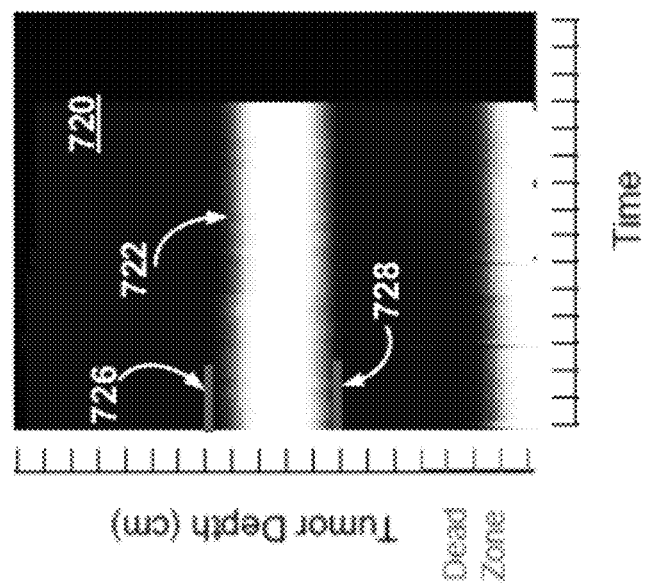
FIG. 7A
FIG. 7B

SYSTEM AND METHOD FOR TUMOR ANALYSIS AND REAL-TIME BIOPSY GUIDANCE

CROSS-REFERENCE TO RELATED APPLICATIONS

The present application claims benefit of and priority from a U.S. Provisional Patent Application No. 61/417,139 titled "System and Method for Tumor Analysis and Real-Time Biopsy Guidance" and filed on Nov. 24, 2010. The entire disclosure of the above-mentioned provisional application is incorporated herein by reference.

TECHNICAL FIELD

The present invention relates to systems and methods for imaging and, more particularly, to systems and methods for tumor location analysis and real-time biopsy guidance using molecular breast imaging.

BACKGROUND OF THE INVENTION

Breast cancer screening has been recommended for many decades, particularly in women over the age of fifty. The combination of early detection and improved therapy of breast cancer in the U.S. has resulted in a significant reduction in breast cancer mortality, with similar reductions being observed in other countries. Despite the success of screening mammography, however, it is also recognized that mammography is a less than perfect screening method. The limitations of mammography are particularly evident when it is used on women having mammographically-dense breasts. It has been shown that the sensitivity of mammography decreases with increasing mammographic density, and is less than fifty percent for women with an extremely dense breast pattern on a mammogram.

The reduction of sensitivity of mammography with the increase of mammographic density is compounded by the fact that increased breast density is a significant risk factor for breast cancer. Given that a dense breast pattern is more characteristic of younger women, this factor significantly diminishes the value of mammography in the screening of young women who have a high familial or genetic risk of breast cancer.

A second major limitation to screening mammography lies in the evaluation of women at high risk of breast cancer. Numerous studies have demonstrated that, when performed on women with a high genetic risk of breast cancer, mammography has a sensitivity of between about 33 and about 43 percent. Most of these studies have been performed with women with an average age of forty, so part of the explanation for the poor performance of mammography in these studies may be due to the presence of dense breast patterns in a significant percentage of the mammographic images.

A possible solution to the problem of the detection of breast lesions in dense breast tissue is to use ultrasound-based techniques with such patients. Ultrasound (US) techniques are attractive for supplemental screening because they are widely available, well-tolerated by patients, and involve no exposure of the patients to radiation. However, while supplemental US screening uncovers more occurrences of breast cancer, it also substantially increases the risk of a "false positive" cancer finding and unnecessary biopsy. Hence, the use of whole-breast ultrasound as a sole identifier of breast malignancies is questionable. Even in combination with mammography, the two anatomical techniques have significant limitations. It would be of considerable benefit to provide another complementary method that offers functional information about lesions available from the results of the US screening. Such a method would significantly reduce the number of "false positive" cases, and allow the radiologist to evaluate those lesions that demonstrate both a functional and anatomical abnormality.

Over the last five years, several nuclear medicine-based technologies have been developed that have application in breast imaging. Included in these are positron emission mammography ("PEM") and molecular breast imaging ("MBI"). In PEM the breast is compressed between two opposing detectors and the 511 keV gamma rays emitted by a positron-emitting radiopharmaceutical, such as F-18 fluoro-deoxyglucose, for example, are detected by coincidence imaging between the two opposing detectors. The PEM images provide an image of glucose utilization by breast tissue and have been shown to be capable of detecting small cancers in the breast. Unlike anatomical techniques such as mammography and ultrasound, PEM is not influenced by dense breast tissue.

The second nuclear medicine-based technique is MBI. This technology employs one or two small gamma cameras. The breast is compressed between a camera and a compression paddle, or between two gamma cameras, and radiation emitted by a single-photon radiopharmaceuticals, such as Tc-99m sestamibi, is detected after collimation. MBI is a planar imaging technique without tomographic capability; however, information from two opposing gamma cameras can be used to calculate the true depth of a functional abnormality in the MBI images. The MBI system has been shown to have a very high sensitivity (for example in some cases greater than ninety percent) for the detection of lesions smaller than ten millimeters across. In addition, it has been found that, in some cases, MBI can detect three times as many cancer occurrences as digital and analog mammography in asymptomatic women at increased risk of breast cancer.

Beyond sensitivity differences, technologies that provide functional images of the breast tissue, such as MBI, can detect lesions not visible with conventional mammography. Likewise, in some cases it may not be practical to co-register and co-analyze anatomical images from one imaging modality, such as ultrasound systems, and functional images from MBI to further facilitate guided biopsies. For example, one might desire to use anatomical images gathered in substantially real time from an ultrasound imaging system to aid in biopsy guidance coupled with MBI images. However, the logistics of such a process would be quite difficult. For example, US imaging typically requires that the patient be supine and that a handheld scanner be used to scan the breast tissue. In comparison, MBI is usually performed with the patient seated and the breast lightly compressed between the gamma cameras or a camera and paddle. MBI employs light compression forces, for example 10-15 pounds of force, with imaging times in the 5-10 minute range. Because of the differences in patient orientation alone between MBI and ultrasound, the shapes of the breast tissue being imaged with the use of these two modalities are significantly different and, hence, the correlation of an anatomical abnormality with a functional abnormality becomes complicated. Therefore, accurate co-registration of anatomical images from ultrasound and functional information from MBI is not currently possible.

It would therefore be desirable to provide a system and method that provides functional images of the breast and enables real-time feedback of interventional procedures.

SUMMARY OF THE INVENTION

Embodiments of the invention provide a molecular breast imaging (MBI) system that includes a generally removable detector head containing a gamma-ray detector and a collimator. The collimator includes multiple collimation sections that have, respectively, different collimation characteristics. In one embodiment, different collimation characteristics include different collimation angles defined, at least in part, by different spatial orientation of holes or channels of corresponding collimating sections. For example, one collimating section may have a collimation angle of about zero degrees (as measured with respect to the normal to a gamma-ray collecting plane of the collimator), and another collimating section may have a collimation angle that is acute (when similarly measured). In a specific embodiment, the collimator has two collimating sections, one of which is adapted to include co-axial conically shaped holes or channels that circumscribe another collimating section.

Embodiments additionally provide an MBI system in which one of the compressing arms is configured to receive a re-attachable elements such as an acoustic coupling element or a biopsy element. In addition, embodiments of the invention may include a display configured to display a first image representing a portion of the breast tissue in spatially-separate regions of the image or a second image including a time-series image containing consecutive image frames updatable in substantially real time based on information acquired from the detector. Alternatively or in addition, the embodiments may include a gantry system supporting the detector head such as to permit relative motions of the detector head about the gantry system.

Embodiments of the invention additionally provide an MBI system that includes an upper compression pad and a lower compression pad. At least one of the compression pads contains a gamma-ray detector and a collimator configured to receive gamma-rays from a region of interest (ROI) of the breast tissue in two areas of the gamma-ray detector, one of which areas continuously circumscribes another area. The collimator includes two sections, one of which is characterized by one collimation angle and another of which is characterized by another collimation angle. One of these two collimating sections has co-axially disposed conical channels oriented circumferentially around another collimating section.

An embodiment of the MBI system may additionally include a disengageable acoustic coupling element, adapted to receive an ultrasound imaging apparatus, or a disengageable biopsy element, adapted to receive and pass a biopsy needle through the disengageable biopsy element towards the collimator. In addition, the MBI system may include a display configured to display a first image of the ROI including a ring image portion and a spot image portion inside the ring portion. Such image represents spatial position of the ROI in the breast tissue, including depth, such that the depth of the ROI in the breast tissue is derivable based on a geometrical parameter of the ring portion of the image. In addition or alternatively, embodiments of the MBI system may include a display configured to display a line image of the ROI in reference to a scale indicating a distance of the ROI from the upper compression pad. Finally, the display of the MBI system may be configured to display an updatable image containing adjoining line images of the ROI, which line images correspond to consecutively dynamically-acquired image frames. Such updatable image represents changes in radioactive activity of the ROI.

Embodiments of the invention also provide a method for performing an image-guided biopsy that includes (i) positioning a portion of tissue to be imaged between two compression members, at least one of which has a gamma-ray detector and a gamma-ray collimator having multiple sections with different collimation characteristics; (ii) initiating a biopsy procedure through one of the compression members; (iii) displaying an image of the portion of the tissue based on information acquired by the gamma-ray detector from gamma rays that have passed through the multiple collimation sections; and (iv) updating the displayed image to provide real-time feedback data representing a status of the biopsy procedure. In one embodiment, the real-time feedback data includes data representing location of a biopsy needle (including depth) with respect to at least one of the compression members. The method may additionally include receiving ultrasound imaging data from an acoustic coupling element coordinated with one of the compression members

BRIEF DESCRIPTION OF THE DRAWINGS

FIG. 3 is an elevational side view and associated top plan view of a conical slant-hole collimator in accordance with an embodiment of the present invention.

FIG. 4A is a perspective, partial cross-sectional view of a conical slant-hole collimator of FIG. 3.

FIGS. 7A, 7B are views of alternative images and image-display configurations provided by of the embodiments of the MBI and collimator systems of FIGS. 1, 3, 4A, 4B configured to provide real-time biopsy guidance using the embodiment of the MBI system of FIG. 1.

DETAILED DESCRIPTION

Figure 1:
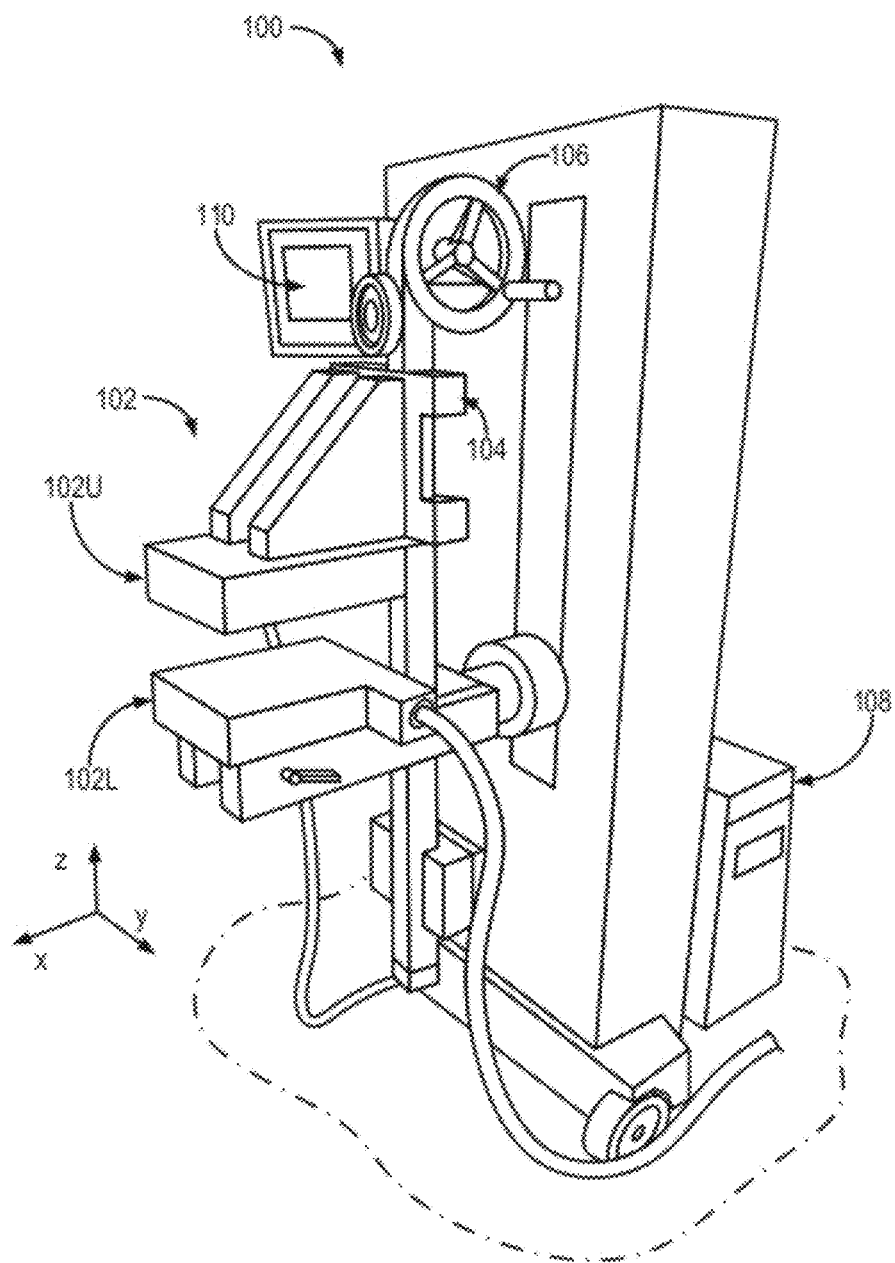
FIG. 1 is an illustration of a molecular breast imaging ("MBI") system according to an embodiment of the present invention.

Referring to FIG. 1, an embodiment of a molecular breast imaging ("MBI") system 100 includes two opposing detector heads 102 containing cadmium zinc telluride ("CZT") detectors. In particular, the detector heads (or detector head assemblies) 102 include an upper detector head 102U and a lower detector head 102L. Examples of MBI systems and methods for their use are described, for example, in a co-pending U.S. patent application Ser. No. 12/515,369, the disclosure of which is herein incorporated by reference in its entirety. Each detector head 102U, 102L is sized to be, for example, 20 centimeters ("cm") by 16 cm (or has a similar size) and mounted on a modified upright type mammographic gantry 104. In one configuration, the detector heads 102 include Lumagem® 3200S high-performance, solid-state cameras from Gamma Medica-Ideas, Inc., having a pixel size of 1.6 millimeters ("mm") (Lumagem® is a trademark of Gamma Medica-Ideas, Inc., Northridge, Calif.).

The relative position of the detector heads 102 can be adjusted using a user control 106. In a related embodiment (not shown), the positioning of the detector heads 102 is controlled with a computer processor. In a specific embodiment, the detector head assemblies 102 are configured to operate as a compression mechanism that squeezes or compresses a breast of a subject between the head assemblies 102U and 102L. Accordingly, this system configuration reduces the maximum distance between any lesion in the breast and either detector head 102U, 102L to about one-half or less of the total breast thickness, thereby potentially increasing the probability and efficiency of the detection of small lesions without additional imaging time or dose. The MBI system 100 includes a processor 108 that is programmable to process the signals and/or imaging data acquired by the detector heads 102 to produce an image, which may be displayed on an associated display 110.

Figure 2:
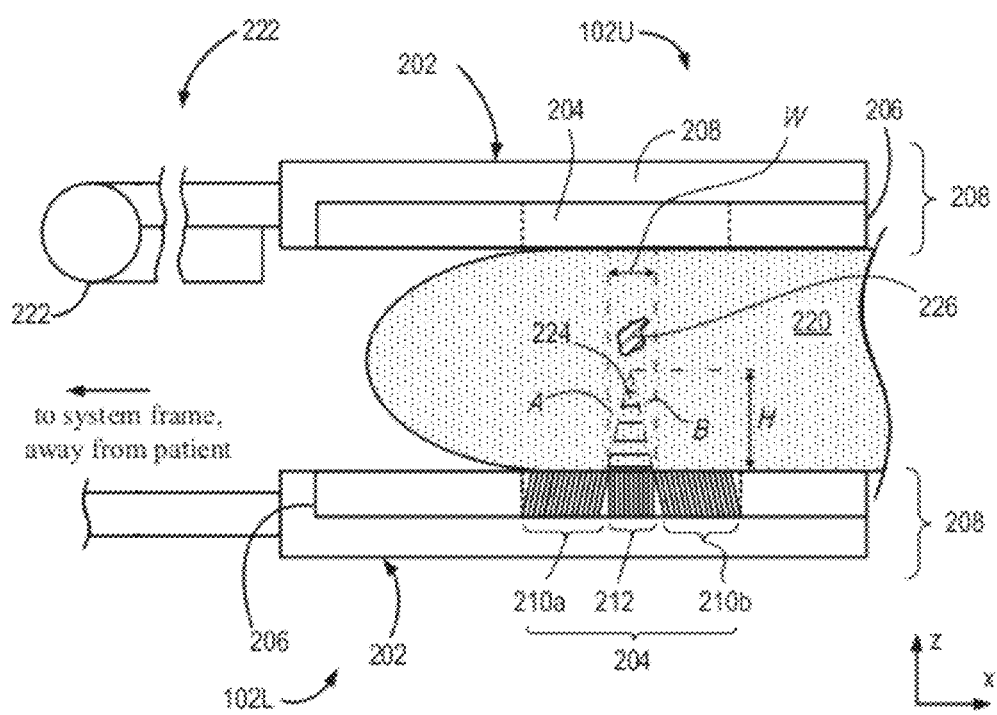
FIG. 2 is a side elevational illustration of the pair of opposed gamma detector heads of the embodiment of FIG. 1 showing a cross-sectional view of an embodiment of a slant-hole collimator having a 2D-varying structure.

Referring to FIG. 2, a two-dimensionally (2D) varying embodiment of the collimator is described. As shown, each of the heads 102L, 102U is not to scale and may include a corresponding gamma-ray detector 202 and an embodiment of the corresponding 2D slant-hole collimator 204 positioned in a corresponding collimator frame 206 next to the corresponding gamma-ray detector 202. While FIG. 2 shows structural details of only the collimator 204 of the lower detector head 102L, the structure of the collimator 204 of the upper detector head 102U (should the head 102U include the collimator) is similar and is not shown here for simplicity of illustration. The collimator frame 206 is appropriately sized to be received by a recessed portion of the detector head 202. The inner extent of the collimator frame 206 is adapted to receive and accommodate the collimator 204 therein, such that the collimator 204 is positioned in spatial alignment with a detector array 208 (such as, for example, a cadmium zinc telluride or CZT detector array) formed in cooperation with a surface of the detector-head 202.

As shown in FIG. 2, the collimator 204 contains three separate collimating sections, 210a, 210b, and 212. The holes or channels of the first and second sections 210a, 210b of the collimator 204 are slanted or inclined with respect to the breast 220, at corresponding angles A and B (not shown) from lateral to medial and vice versa. At the same time, within the corresponding region 210a or 210b, the holes of channels are mutually parallel, from chest wall to nipple. In one embodiment, the measures of angular inclination (and corresponding collimation angles of sections 210a, 210b) A, B may be opposite in signs but equal in absolute value. Generally, as measured with respect to the normal to the gamma-ray collecting surface of the collimator 204, the angles A, B are acute (in one embodiment, for example, 30 degrees) or, as measured with respect to the gamma-ray collecting plane of the collimator 204, obtuse. Similarly, the holes or channels of the third section 212 extend vertically (i.e., normally with respect to the gamma-ray collecting surface of the collimator 204) across the breast 220 from lateral to medial and vice versa and, at the same time, are mutually parallel across whole the region 212 from chest wall to nipple. The collimating section 212, therefore, is characterized by a collimation angle of substantially 90 degrees as measure with respect to the gamma-ray collecting plane of the collimator 204. The structure of the collimator 204 has, therefore, a 2D-varying geometry: the structure of either of the sections 210a or 210b with section 212 of the collimator 204 remains the same as viewed in any cross-sectional plane that is parallel to the xz-plane of FIG. 2, and remains substantially unchanged along the y-axis of FIG. 2.

In comparison with a traditional collimator that contains a single collimating section, the holes or channels of which are directed substantially perpendicular to the plane of a supporting detector head (for example, to the plane of the head 102L or xy-plane), the embodiment 204 is characterized by an approximately two-fold increased sensitivity and, in addition, permits estimation of the depth of the lesion 226 within the breast tissue 220. As discussed further below, the assessment of lesion depth in the breast 220 is effectuated by considering the relative distances to the lesion as reflected by portions of the image that are respectively associated with the collimating sections 210a, 210b, and 212 of the collimator 204.

Specifically, and in further reference to FIG. 2, the three-sectional structure of the collimator 204 defines a "dead" or "dark" zone denoted in a cross-sectional view of FIG. 2 as a triangular area 224. The terms "dead" or "dark" refer to the fact that the zone 224, while visible by central collimating portion 212, is not visible by the peripheral collimating portions 210a, 210b. More particularly, the zone 224 is defined above the central collimating portion 212 and is bounded by the planes containing, respectively, the holes or channels of the sections 210a, 210 that are closest to the section 212. It is appreciated that a portion of the breast tissue 220 that is located substantially within the bounds of the zone 224 is imaged through the central collimating section 212 but is not imaged through the collimating sections 210a, 210b containing the slanted holes or channels. Indeed, imaging gamma rays that propagate through the breast 220 from the upper detector-head 102U downwards, in a –z direction towards the detector-head 102L and within the bounds of the central collimating section 213, are generally not received and propagated by either of the collimating sections 210a and 210b because these gamma rays are outside of the corresponding fields of view of the collimating sections 210a, 210b. The optional collimator 204 of the upper detector-head 102U, which is similarly configured, also has a corresponding "dead" imaging zone. For A=B, the height H of the "dead" zone is defined by the width W of the central collimating portion 212 and the slant or inclination angle A via W=2H·tan A. For example, a central collimating section having a width of W=2.3 cm defines the height of the dead zone to be about H=2 cm.

The formation of the "dead" zone 224 due to slanting the holes or channels of the side collimating zones 210a, 201b with respect to those of the central collimating zone 212 and a corresponding increase in spatial resolution along the z-axis can be advantageously utilized to reduce the likelihood that a biopsy needle, inserted into the breast 220 from above, will penetrate through the lower side of the breast 220 and impact the collimator 204 of the lower detector head 102L. Accordingly, the risk of contaminating a biopsy needle with lead from the collimator and introducing these contaminants into the breast 220 is controlled. It is appreciated that an image, of a lesion 226 that is outside of the "dead" zone, formed by the collimator 204 of FIG. 2 includes three spatially-separate and localized in xy-plane image portions formed according to inclination angles A,B through respectively corresponding collimating sections 210a, 212, and 210b. Therefore, is a particular lesion is seen only at a portion of the image attributable to the central collimating section 212 of the collimator 204 and not at a portion of the image attributable to the collimating sections 210a, 210b, such lesion is located within the "dead" zone 224 of the collimator 204. A lesions within the "dead" zone of the collimator is considered to be located too closely to the lower detector head 102L for desirable biopsy. In this case, the breast 224 and the detector heads 102U, 102L can be mutually repositioned so that the lesion 226 is outside of the "dead" zone and, as a result, not in as close proximity to the lower detector head 102L.

A related embodiment of a conical slant-hole collimator of the invention, discussed further in reference to FIGS. 3, 4A, 4B, and 5. FIG. 3 shows a portion of an embodiment 304 of the conical slant-hole collimator in both partial top plan view and a corresponding cross-sectional elevated view. The embodiment 300 includes a three-dimensionally (3D) varied geometry that is configured, as will be described, to gain localized spatial resolution along a direction of propagation of imaging gamma-rays (i.e., along the z-axis) as compared to a conventional, parallel-hole collimator. Moreover, the sensitivity of the embodiment 300 is also increased as compared to a conventional, parallel-hole collimator, because the number of holes of channels of the collimator 300 receiving imaging gamma-rays that have traversed the lesion 226 is larger than in the case of the parallel-hole collimator. In addition, the three-dimensionally (3D) variable geometry of an embodiment of a collimator of the present invention is adapted to facilitate the ability of the system to provide real-time (generally, under a minute) visualization of the position of both a lesion in question and a radiolabeled needle. This, in turn, enables a radiologist to carry out the biopsy procedure (insert a needle into the lesion) without the need to wait several minutes for the acquisition of a confirmatory image. In comparison with the embodiment 204 of FIG. 2, the collimator 300 also includes a plurality of collimating sections 310, 312 having differing characteristics. Specifically, it is contemplated that the differing characteristics of the plurality of collimating sections 310, 312 may include differing collimation angles. The collimating section 310 is configured to circumscribe the centrally located collimating section 312.

Specifically, the structure of the central collimating section 312 is generally similar to that of the central collimating section 212 of FIG. 2 in that the section 312 of FIG. 3 includes a plurality of directional holes or channels aligned in a mutually parallel fashion generally perpendicularly to a gamma-ray-collecting surface 316 of the collimator 300. The holes or channels 302 of the peripheral collimating section 310, on the other hand, are configured to be conically shaped and positioned in a co-axial fashion such as to form concentric circles when viewed from above the gamma-ray-collecting surface 316. In a cross-sectional plane that is perpendicular to the gamma-ray-collecting surface 316 and contains a diameter of any of these concentric circles, the holes or channels 302 are seen, therefore, to inclined or slanted at a generally acute angle A, as measured with respect to the normal to the gamma-ray collection plane 316 of the collimator 300. The ellipses 320 indicate portions of the collimator 300 not explicitly shown in the views of FIG. 3.

Configuring an embodiment of the invention to include the above-mentioned conical slant-hole collimator section 310 and a vertical-hole collimation section 312 encircled by the section 310 offers additional operational advantages. Specifically, in comparison with the embodiment 204 of the collimator of FIG. 2, and given equal inclination angles A in both embodiments, the embodiment 300 achieves a factor of 5 to 10 gain in sensitivity.

As best illustrated in FIGS. 3 and 4A, it is contemplated that in one embodiment, at least the holes or channels 302 of the first, peripheral collimating region 310 may be further divided by including septa 330. The septa 330 are oriented, for example, in a radial fashion and distributed along the annular holes 302. In one embodiment, the surfaces of the septa 330 are substantially perpendicular to the surfaces of the walls 304. While FIG. 3 illustrates the presence of the septa 330 only in one annulus of the first collimating region 310 for simplicity of the illustration, it is understood that septa may be generally formed in any hole or channel 302 at any position in the collimating section 310. Likewise, as illustrated in FIG. 4A, it is contemplated that the second, central collimating region 312 may also include at least one septum 336 disposed in at least one of the vertically-oriented holes of channels 306. Generally, the septa are configured to subdivide a given collimating hole or channel to which they belong into collimating sub-channels.

Figure 4B:
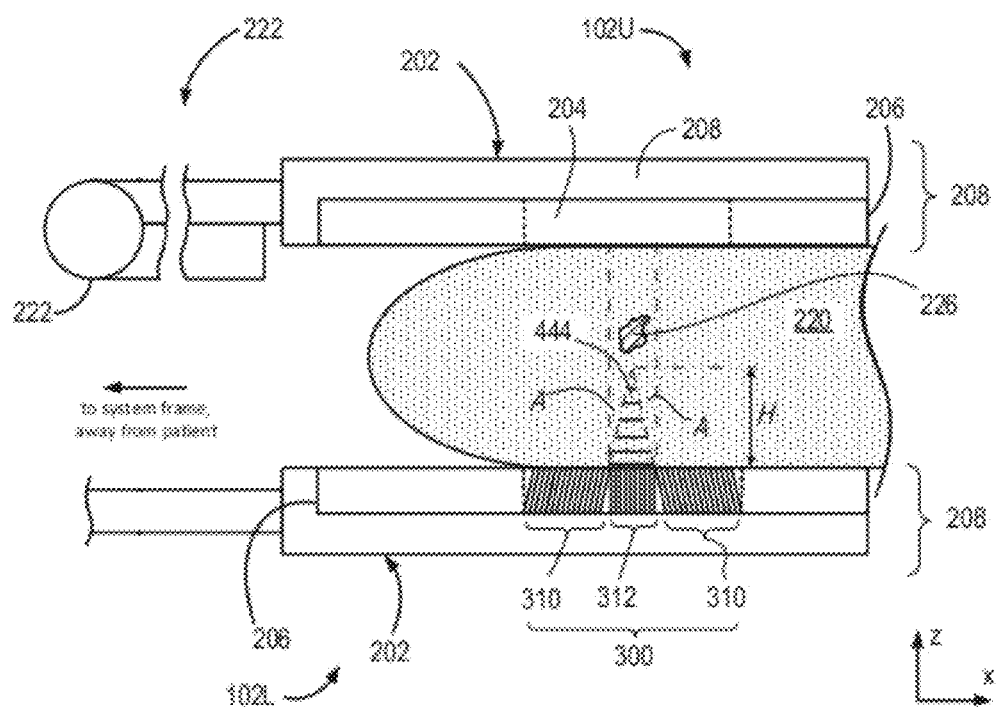
FIG. 4B is a side elevational illustration of the pair of opposed gamma detector heads of the embodiment of FIG. 1 showing a cross-sectional view of the embodiment of a conical slant-hole collimator of FIG. 3.

In further reference to FIG. 3 and referring to FIG. 4B, for imaging with the use of a conical slant-hole collimator, the breast 220 of a patient is positioned, again, between the detector heads 102U and 102L, at least one of which (for example, the head 102L) contains the collimator 300 in the collimator frame 206, and is lightly compressed therebetween. In a fashion similar to that described in reference to FIG. 2, a conical slant-hole collimator 300 also has a "dead" zone 444 associated with it. The "dead" zone 444 is substantially defined by a volume between the conical surface associated with the wall of the innermost hole 302 of the peripheral collimating section 310 and the gamma-ray collecting surface 316. A portion of the breast tissue located within such "dead" zone will be imaged substantially only by the central collimating section 312 and not by a peripheral collimating section 310.

Figure 5:
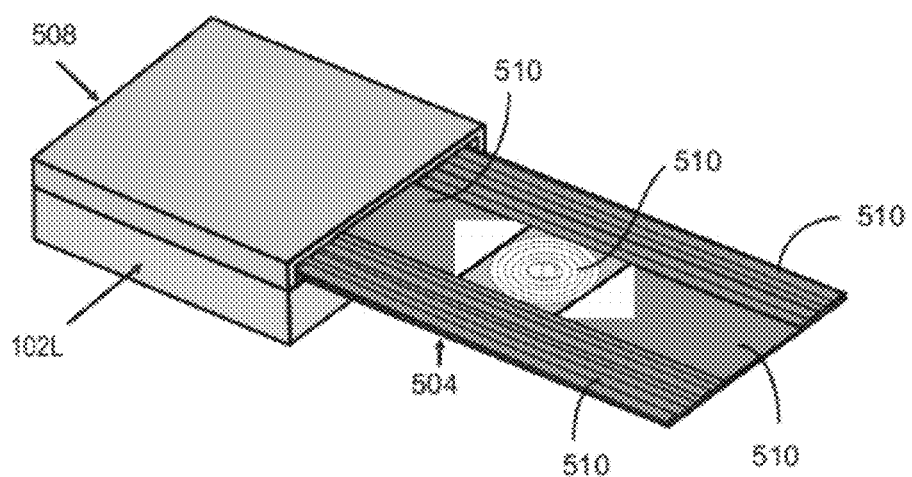
FIG. 5 is a perspective view of a system configured to repositioning of the conical slant-hole collimator of FIG. 3 in cooperation with a detector head according to an embodiment of the present invention.

In clinical use, the embodiment of the conical slant-hole collimator would be positioned directly underneath the lesion to be biopsied. FIG. 5 shows a portion 500 of the collimator repositioning system containing the embodiment 300 on a tray 504 that is configured to be slidable into a collimator sleeve 508. Lead plates 510 adjacent the collimator 300 on the tray 504 are positioned to limit the field-of-view of the detector (not shown) under the collimator 300 to that corresponding only to an area of the collimator 300. In use, the tray 504 is caused to slide into the sleeve 508 and is positioned beneath the lesion. For lesions located close to the chest wall (within approximately half the diameter of the conical collimator from the chest wall), a semi-circular version of the collimator (containing a left half of the collimator 300 as presented in FIG. 3) would be utilized to gain access to this part of the breast. While possessing only half the sensitivity of the full conical slant-hole collimator 300, the use of such half-conical slant-hole collimator will permit biopsy of lesions close to the chest wall.

Figure 6B:
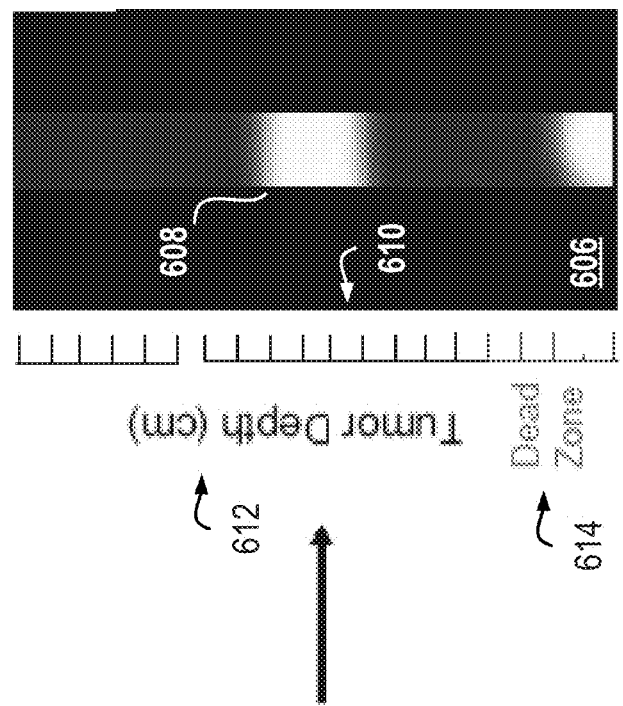
FIGS. 6A, 6B are examples of an image and an image-display configuration provided by the embodiments of the MBI and collimator systems of FIGS. 1, 3, 4A, and 4B.
Figure 6A:
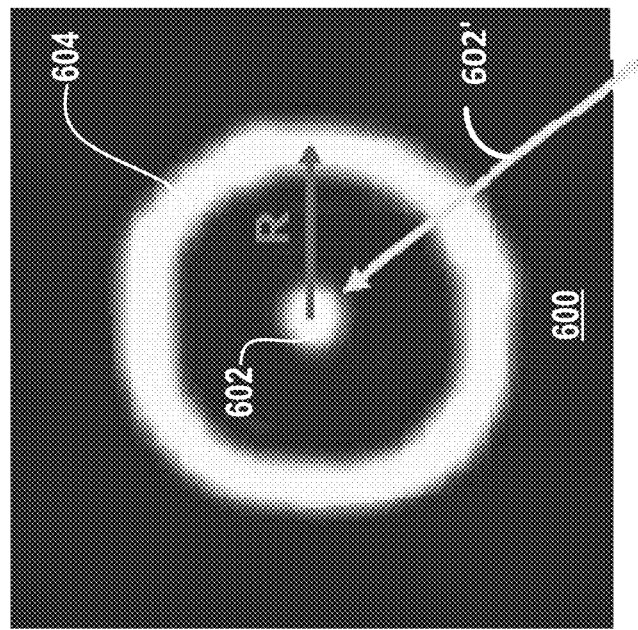

FIG. 6A shows an example of an image 600, of the lesion 226 located in the breast 220 outside of the "dead" zone of the collimator 300, that has been simulated with the use of the system of FIG. 4A. It is understood that the central collimating portion 312 of the collimator 300 is configured to deliver gamma-rays to a first, central area of the detector array 208, the peripheral collimating section 310 of the collimator is configured to deliver gamma-rays to a second area of the detector that circumscribes or is extended circumferentially, around the first area and that is separated from the central area of the detector by an annular region. Accordingly, a pattern of gamma-rays delivered by the collimator 300 to the detector array 208 includes two spatially-separate gamma-ray pattern portions, one of which encircles another. As a result, in the image 600, the lesion 226 appears as a combination of a "hot spot" image portion 602 (pointed to with an arrow 602') and a "ring" image portion 604 encircling the "hot spot" portion 602. The "hot spot" 602 corresponds to imaging of the lesion 226 with the central, vertical-hole collimating section 312 of the collimator 300, and a "ring" image portion 604 corresponds to imaging of the lesion 226 with the peripheral, conical slant-hole collimating section 310 of the collimator 300. The depth of the lesion's location within the breast 220 can be calculated from the diameter (or radius) of the "ring" 504.

In order to view a lesion at a depth of 6 cm, for example, and assuming the collimation angle A=30°, the peripheral collimating section 310 of the collimator 300 would need to be approximately 6.9 cm in width (2×6 cm×tan 30°). A conical collimator configured according to the embodiment 300 of the invention would be about 7-9 cm in diameter.

Interpretation of an image such as the image 600 of FIG. 6A, may not be intuitive because the system employing the conical slant-hole collimator 300 may, in some cases, have a somewhat reduced spatial resolution in a plane of the detector (i.e., in an xy-plane) as compared with a conventional, parallel-hole collimator has holes or channels oriented substantially parallel to a direction of propagation of gamma-rays (i.e., along the z-axis), because a portion of gamma-rays that have traversed the lesion 226 are now directed to the detector by the conical section 310 and, therefore, give rise to image data representing axial position of the lesion 226 along the z-axis. Stated differently, the collimator 300 of the lower detector head 102L, because of its varied geometry, allows to counterintuitively gain localized resolution of imaging in a third dimension along with the ability to provide real-time feedback at, possibly, some expense of the conventional resolution in only two dimensions afforded by a parallel-hole collimator. It is appreciated that the portions 602 and 604 of the image 600 both include image information about a local area, of the imaged breast 220, defined by the lesion 226 that is outside of the "dead" zone 444 of the collimator 300 and the surrounding tissue that is also outside of the "dead" zone 444. Such local area, therefore, is "spatially displaced" in the process of imaging in the image 600 to be reflected in both the hot spot 602 and the ring 604). Based on this realization, one can track a biopsy needle with a radio marker as the needle is guided from the top of the breast toward the tumor 224 by continuously updating the image 600 in real time and ensuring that the imaged needle remain centered on the "hot spot" 602 while moving inward from the "ring" 604 toward the "hot spot" 602. In this regard, localized spatial resolution is provided in a two-dimensional image 600 in three dimensions by way of the relative position of the needle with respect to the hot spot 602 (resolution in xy-plane) and with respect to the ring 604 (resolution along the z-axis).

In addition, by visualizing the data reflected in the image 600 differently, real-time feedback for interventional procedures can be readily achieved in another, highly-intuitive form. It is contemplated that a center of mass determination of activity about the hot spot 602 can be used during the biopsy process to verify that the lesion 226 has not shifted during biopsy due to patient motion or movement of the tumor within the breast during the biopsy process. Specifically, radial summation of the image intensity around the ring 604 is performed to convert the initial image 600 into a single vertical line image 606 of FIG. 6B. In this image 606, the ring 604 of FIG. 6A now appears as a single area 608 of increased activity on a vertical scale 610. The scale 610 is appropriately calibrated to indicate the depth of the lesion (or its separation) from the upper detector head or paddle 102U in area 612, and to indicate s the "dead" zone 444, where performance of needle biopsy is problematic, in area 614. In a related embodiment, the scale 610 could be appropriately inverted to indicate the depth of the lesion (or its separation) from the lower detector head 102L, if in the system of FIG. 4A the collimator 300 is engaged with the upper detector head 102U instead of being engaged with the lower detector head 102L.

With the above-described configuration, when the acquired image is updated in real time, biopsies are performed with the data being acquired in a dynamic mode. Referring to FIG. 7A, at user-determined frame rate (typically every 5-15 seconds depending on type of activity), each image frame of the dynamic image acquisition is summed and displayed next to the previous image frame to form a series of images of consecutive image-frames. In this way, a time-series image 720 is provided that resembles an "ECG-type" display trace showing the location of the lesion 226 and any other radioactive source in the field of view of the conical collimator 300. Using this time-series image display scheme, any change in the quantitative estimate of lesion activity can be determined. For example, changes in a portion of the image-trace 722 (such as its width or intensity, for example) are useful in determining if the biopsy process successfully removed any part of the imaged breast tumor. Within a tumor-related area defined by a pair of lines 726, 728 of the time-series image 720, the produced image information can be utilized in a number of ways. For example, measurement of the center of mass of activity of such area can be used to monitor a movement of the tumor. Summation of activity within the tumor-related area can be used to generate a display 724 of activity and, therefore, enable the user to distinguish a change in activity due to partial removal of the tumor rather than that due to a movement of the tumor outside the central field of view. For example, reduction in tumor activity with no change in the center of mass would be consistent with the tumor removal. In comparison, reduction in tumor activity accompanying a change in location of the center of mass would be consistent with movement of the tumor. This is an advantageous check, as it is possible for the patient to move, or for the lesion to be displaced by the needle during the biopsy process.

In addition, it is contemplated that the biopsy needle or other locator similar to the introducer in MRI biopsy systems, may contain an intense source of radioactivity at a lower energy than that emitted by the radiopharmaceutical located in the lesion (e.g. I-125 seed source, Tl-201 source). Accordingly, images of the needle would not interfere with images of the lesion, but could be processed in a similar manner and superimposed on the vertical trace image to provide the radiologist with real-time feedback on the location of both the lesion and the biopsy needle or locator.

The above-described embodiments of a system and method for real-time MBI guided biopsy of the breast also enable simultaneous MBI/ultrasound imaging of the breast tissue. This system provides a more complete imaging solution for women with dense breast tissue where the sensitivity of mammography is known to be limited, and does so in a cost-effective manner that permits its widespread adoption into clinical practice.

In a conventional configuration, imaging information is typically obtained sequentially from the two imaging modalities and some motion or movement of the breast between the two imaging processes may occur. However, the proposed configuration is beneficial in that the location of a lesion that is not visible on a conventional ultrasound image can be determined and indicated on a MBI image, and may also be identifiable from enhanced ultrasonic techniques, such as elastography, thereby permitting ultrasound-guided biopsies if desired. In practice, in a high percentage of cases (for example, greater than eighty percent), a lesion can be seen on just the lower MBI detector; thus, during ultrasound imaging, information on the location of the lesion can be updated on the ultrasound system to confirm that the location of a lesion has not shifted in the conversion from MBI to ultrasound imaging modes.

Referring again to FIGS. 1, 2 and 4B, imaging of the breast 220 is performed using the aforementioned MBI system embodiment 100 of FIG. 1 that includes, in relevant part, a set-up of FIG. 4A. The results of such imaging which permit a calculation of an in-plane (x and y) location of a lesion in the breast 220 as well as its depth (relative position along the z-axis), and relative uptake of an administered radionuclide. In one embodiment, As illustrated in FIG. 4B and further described below in reference to FIGS. 8 and 9, the upper detector head 102U may be affixed to a rotatable gantry arm, which provides a rotation of the upper detector head 102U (for example, in the xz-plane, about a hinge 222) and facilitates interchangeability of the upper detector head 102U with other functional components devices, such as an ultrasound system, for example.

Figure 8:
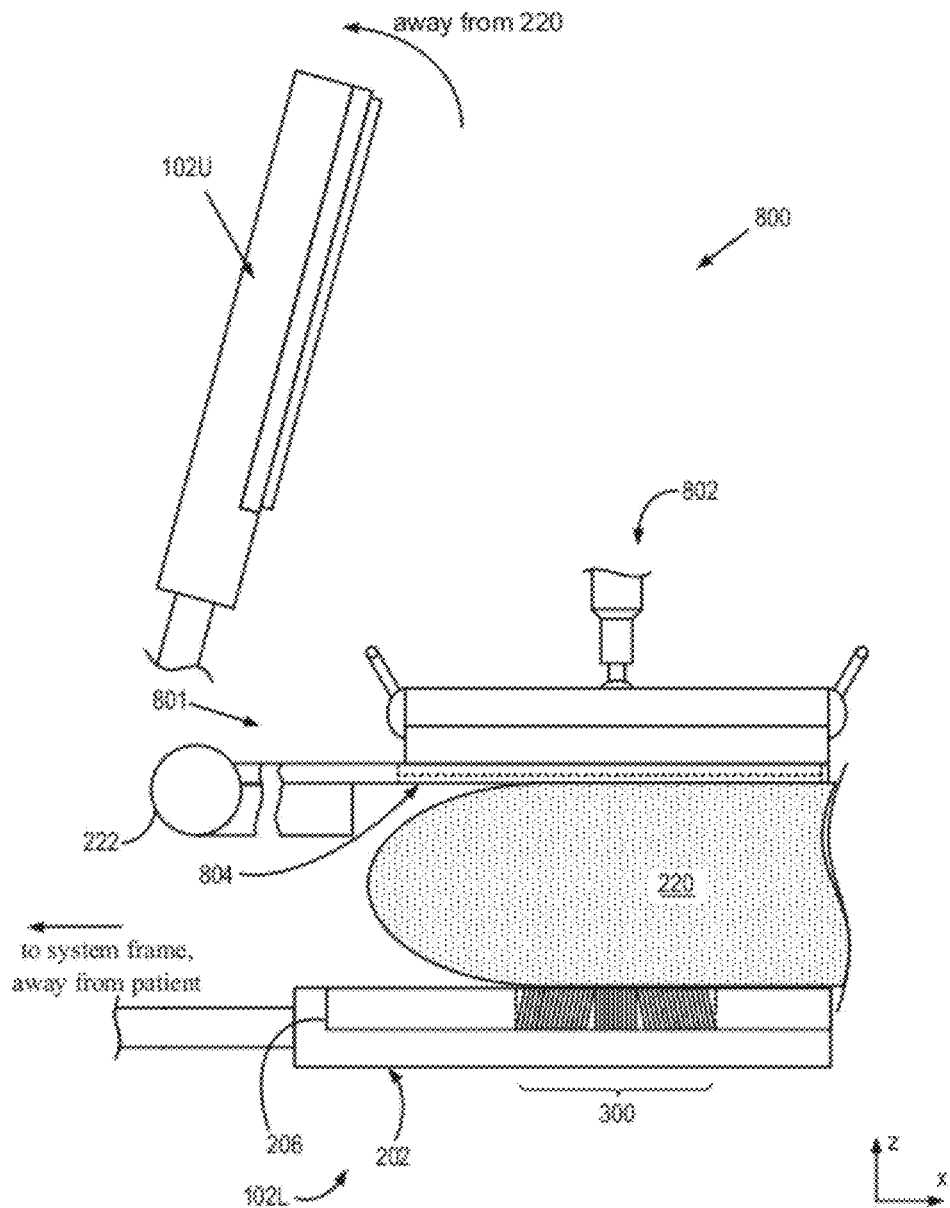
FIG. 8 is a side elevational view of a reconfigurable embodiment of the system in which a gamma detector head is replaceable by an ultrasound system.

In particular, FIG. 8 shows a reconfigurable embodiment 800 of the invention configured to facilitate imaging of breast tissue with multiple modalities. As shown, the upper detector head 102U is adapted to be disengageable from the remaining portion of the MBI system to be replaced by another system such as, for example, an ultrasound system 801 that, for example, may include a WUS sub-system 802 having an ultrasound paddle dimensioned similarly to the upper detector head 102U. An acoustic coupling plate 804 of the US system 801 is designed to provide a contact surface for receiving and compressing a portion of a subject under examination (such as a portion of the subject's breast 220). In the described reconfigurable embodiment 800 of the MBI/WUS system, the WUS sub-system 802 acts as one part of a compression device to lightly compress breast 220 between the WUS system 802 and the lower MBI detector head 102L. The acoustic coupling plate 804 is composed of a material with low acoustic attenuation, and is preferably composed of a material with ultrasonic reflective properties that are similar to those of a soft tissue. Examples of appropriate materials include nylon and latex. The acoustic coupling plate 804 is adapted so as to permit the passage of a biopsy needle through the acoustic coupling plate 804 and into the breast 220. For example, a nylon mesh can be employed and manufactured with a grid of holes to allow a needle to be passed through for creast biopsy. Additionally or in addition, the acoustic coupling plate 804 is adapted to retain the breast 220 in a compressed position prior to retraction of the upper detector head 102U.

Examples of WUS sub-systems that can be used with embodiments of the invention include a combined ultrasound probe and compression paddle device marketed under the trademark SomoVu™ (U-Systems, Sunnyvale, Calif.). The WUS sub-system 802 is normally designed to be placed directly on the breast tissue with the patient supine. The operator can then perform an automated scan of the breast.

In addition or alternatively, it is contemplated that an embodiment of the reconfigurable MBI-ultrasound system such as the embodiment 800 possesses the capability for elastography on the ultrasound system. Examples of usable systems include an ultrasound probe with elastography capability marketed under the trademark Aixplorer™ (Super-Sonic Imagine, Aix-en-Provence, France). The Aixplorer is normally designed to be placed directly on the breast tissue with the patient supine. In the described configuration 800 of FIG. 8, the Aixplorer probe (not shown) is placed on top of the acoustic coupling plate 804, and shearwave elastography is performed over the region of abnormal uptake identified in the MBI images.

In operation, and in further reference to FIG. 8, the patient is seated and the breast is lightly compressed by the WUS system 802 and lower MBI detector head 102L, in the orientation similar to that of the mammography procedure. Functional imaging of the breast is performed using the MBI system (for example, with the conical slant-hole collimator 300) and, simultaneously or sequentially, the WUS system 802 is operated to complete a sweep across the breast 220 to obtain 3D images of the breast tissue. Upon completion of both image acquisitions, the MBI and WUS images may be co-registered. Advantages of the proposed embodiment include reduced scan time due to the simultaneous acquisition of both the MBI and WUS images, and reduced likelihood of motion artifact causing misregistration. In addition, when using the systems described above with respect to FIGS. 3, 4A, 4B, 5, 6A, 6B, 7A, 7B, the configuration of FIG. 8 can also provide depth-resolved information about the location of a lesion.

Figure 9A:
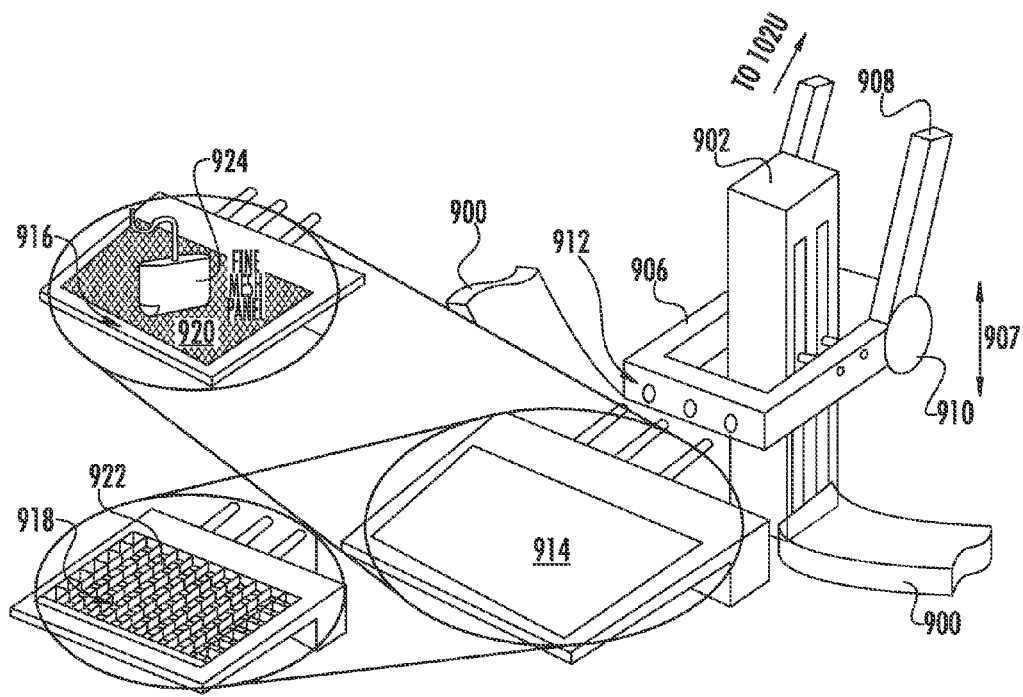
FIG. 9A is a perspective view of an alternative embodiment, including a gantry-based support system, for use with the embodiments of systems of FIGS. 1-8.
Figure 9B:
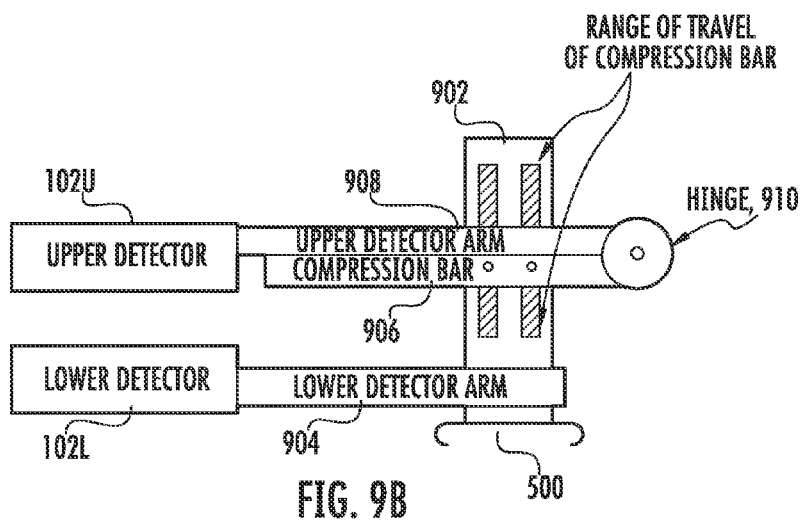
FIG. 9B is a side, elevational view of the embodiment of a gantry-based support system of FIG. 9A.

Referring to FIGS. 9A and 9B, the examples of structural details of the above-referenced embodiment 800 of a reconfigurable MBI/WUS system are discussed. The embodiment 800 may be mechanically articulated, as shown, with a gantry 900, such as that identified as a "Giotto gantry" and available from IMS of Bologna, Italy. A central column 902 is mounted on the gantry 900. Extending from the central column 902 is a lower supporting arm (or lower detector arm) 904 that, in the illustrated configuration, holds the lower detector head 102L in a fixed position. Another, intermediate arm includes a compression bar 906 connected to the central column 902 and to an internal motor (not shown) that drives and repositions the compression bar 906 along central column 902, as shown schematically with an arrow 907. Yet another upper supporting arm (or upper detector arm) 908 is pivotally connected, at its proximal end, to the intermediate arm (compression bar 906) through a hinge 910. Opposite the hinge 910, the upper supporting arm 908 is engaged at its distal end with the upper detector head 102U, as described above.

FIG. 9A shows the embodiment of the system with the upper arm 908 and the compression bar 906 in an open position, when the upper arm 908 is pivoted away from the compression bar 906 such that the upper detector head 102U is out of view and out of operable communication with the breast tissue. In comparison, FIG. 9B shows the embodiment with the upper supporting arm 908 and the compression bar 906 in a closed, mutually adjoining position, when the upper supporting arm 908 and the compression bar 906 are engaged and, optionally, locked together to achieve proper breast compression with the upper detector head 102U. The hinge 910 may be spring-loaded so that some user-applied compressing force is needed to engage the upper detector arm 908 to the compression bar 906. Such loading reduces the likelihood of the upper supporting arm 908 being dropped too abruptly onto the compression bar 906, as the spring absorbs some of the weight of the upper detector head 102U and upper detector arm 808. As mentioned above, the movement of the compression bar 906 along the central column 902 is used to compress the breast tissue between the upper and lower detector heads 102U, 102L.

The open position and/or orientation between the upper arm 980 and the compression bar 906 of the orientation in which an embodiment of the system may be utilized for both combined MBI/ultrasound imaging and for MBI-guided breast biopsy. In one embodiment, for example, the compression bar 906 is adapted to removably receive at least one auxiliary component. To this end, the compression bar 906 is equipped with several locating holes 912 configured to receive an attachable device such as a new compression paddle or device 914. For example, the acoustic coupling plate 804 described above in reference to FIG. 8, or other functional components could be removably engaged with the compression bar 906 via the locating holes 912.

For example, as further shown in FIG. 9A, two types of paddles 916, 918 are contemplated for use with the compression bar 906. The first paddle 916 includes a central section covered with a thin acoustically-transparent mesh 920. When the paddle 916 is cooperated, as a device 914, with the compression bar 906 and the breast tissue (not shown) is compressed between the detector head 102L and the paddle 916, an ultrasound probe 924 can be acoustically coupled to the compressed breast tissue through the mesh 920. The precise location of a lesion derived from the image registered, as described above, with the MBI detector head 102L can be used to properly position the ultrasonic probe 924 with respect to the mesh panel 920 and to permit co-registration of the MBI and ultrasonic images. In one implementation, for example, such positioning of the ultrasonic probe 924 can be achieved by marking the mesh 920 with a grid pattern appropriately labeled to match locations on the MBI images. The coordinates of the lesion location on the MBI image can then be used to determine the appropriate co-registered position of the ultrasound probe 924 on the mesh 820. In another implementation, the location of the lesion on the MBI image may be electronically entered into the ultrasound system and an electronic mark on the ultrasound image may be further used to direct the positioning of the probe 924 with respect to the mesh 920 and to confirm co-registration of the MBI and ultrasound information.

Another paddle 918, for use as the attachable device 914 with the compression plate 906, includes a central section formed of a set of guide holes 922 appropriately configured for biopsy procedures. Here, again, the location on the MBI image can be used to determine the location for the biopsy needle to be placed through the guide holes 922. Real-time imaging, such as described above, may be used to determine depth information and track the location of a lesion, which may shift during the biopsy process.

The present invention has been described in terms of one or more preferred embodiments, and it should be appreciated that many equivalents, alternatives, variations, and modifications, aside from those expressly stated, are possible and within the scope of the invention.

The invention claimed is:

1. A molecular breast imaging (MBI) system comprising:
a first detector head including a first collimator and a first gamma-ray detector configured to receive gamma-rays from a portion of a subject arranged proximate the first collimator, the first detector head being an upper detector head of the MBI system; and
a second detector head including a second collimator and a second gamma-ray detector configured to receive gamma-rays from the portion of the subject arranged between the first collimator and the second collimator, the second detector head being a lower detector head of the MBI system, the first detector head being repositionably opposed to the second detector head such as to compress, in operation of the MBI system, a tissue between the first and second detector heads;
wherein at least one of the first collimator and the second collimator include multiple collimation sections,
each of said multiple collimation sections including multiple collimator channels,
said multiple collimation sections having respectively different collimation characteristics such that a first collimation section from said multiple collimation sections (i) includes multiple collimator channels outputs of which are arranged along circles that are concentric about an axis as viewed along the axis, and (ii) defines conical collimation having multiple foci that are arranged on and separated from one another along said axis,
and
wherein said MBI system is configured to generate a first visual representation of a region of said tissue, said first visual representation having a first annular portion and a second visual representation of a biopsy needle when the needle is inserted in said tissue, said second visual representation having a second annular portion, to enable guiding of the biopsy needle through said tissue and towards said region based on visual comparison of the first and second annular portions.

2. An MBI system according to claim 1, wherein said multiple collimation sections of at least one of the first and second collimators include:
a central collimation section having a collimation angle of approximately 90 degrees relative to first and second parallel surface planes defined by and common to said multiple collimation sections; and
a periphery collimation section having a collimation angle that is obtuse relative to said surface planes.

3. An MBI system according to claim 2, wherein the periphery collimation section includes a collimation section adapted to have conical geometry.

4. An MBI system according to claim 1, wherein the multiple collimation section include a first collimating section containing conical slant-holes all of which are inclined at the same angle with respect to a surface of said at least one of the first and second collimator, and a second collimating section containing vertical slant-holes that are perpendicular to said surface, the second collimating section configured to circumscribe the first collimating section.

5. An MBI system according to claim 1, wherein the first detector head is configured to be removably engaged with the MBI system.

6. An MBI system according to claim 5, further comprising an acoustic coupling element configured to engage with the MBI system when the first detector head is disengaged from the MBI system to receive an ultrasound imaging apparatus.

7. An MBI system according to claim 1, further comprising a display system operably that is connected with a detector head and that displays, in operation of said MBI system, at least one of
(a) the visually-perceivable representation of an identified portion of the breast in spatially separate image regions that include
said ring that is defined by collimation, with the first collimation section, of gamma-rays received from said identified portion of the breast, wherein a depth of said identified portion of the breast is determined based on a radius of the ring,
and
said spot that is defined by afocal imaging, with a second collimation section, of said identified portion of the breast in gamma-rays received therefrom, the spot located in the center of said ring
and
(b) a time-series image-trace containing consecutive image frames updatable in substantially real time using information acquired from at least one of the first detector and the second detector.

8. An MBI system according to claim 1, further comprising a gantry system supporting the first detector head and the second detector head to enable relative motion of the first and second detector heads about the gantry system.

9. A molecular breast imaging (MBI) system comprising:
an upper compression pad; and
a lower compression pad including a gamma-ray detector and a collimator configured to deliver gamma-rays from a region of interest (ROI) of breast tissue onto a gamma-ray detector in a pattern that includes first and second spatially-separate pattern regions,
wherein the second pattern region circumscribes the first pattern region to define conical collimation, wherein all of collimator channels forming said second pattern region are inclined at the same angle with respect to a surface of the collimator, and
further comprising a display operably connected with the gamma-ray detector and configured to display an image-trace of the ROI including
(i) a ring image portion defined by collimation of gamma-rays received from the ROI with collimator channels that form the second pattern region, and
(ii) a spot image portion inside the ring image portion, said spot image portion defined by collimation of gamma-rays received from the ROI with collimator channels that form the first pattern portion,
wherein said image-trace represents a spatial position of the ROI in the breast tissue including depth,
wherein said depth of the ROI in the breast tissue is derived based on a product of a radius of the ring image portion and a trigonometric function of said angle at which collimator channels are inclined.

10. An MBI system according to claim 9,
wherein said collimator includes a first collimating section characterized by a first collimation angle and a second collimating section characterized by a second collimation angle,
the second section having conical channels oriented circumferentially around the first collimating section such as to define multiple foci of said collimator that are arranged on and separated from one another along an axis perpendicular to the surface of the collimator.

11. An MBI system according to claim 9, further comprising at least one of
a disengageable acoustic coupling element, adapted to receive an ultrasound imaging apparatus,
and
a disengageable biopsy element, adapted to receive and pass a biopsy needle guided therethrough in real-time, based on information derived from said image-trace, to a target depth defined by the depth of the ROI towards the collimator.

12. An MBI system according to claim 9, wherein said display is configured to display
a line image of the ROI and
a scale, in reference to which the line image is displayed,
the scale indicating a distance of the ROI from the upper compression paddle,
the line image formed by a conversion of said ring image portion and said spot image portion, wherein said conversion includes radial summation of intensity values of said ring image portion around said ring portion,
in which line image a result of the conversion of said ring image portion appears as a single area of increased activity on said scale.

13. An MBI system according to claim 12, wherein said display is further configured to display time-series image containing adjoining line images, of the ROI, corresponding to consecutively dynamically acquired image frames, said time-series image representing changes in radioactive activity of the ROI with time.

14. An MBI system according to claim 7,
wherein the first detector head is configured to be removably engaged with the MBI system and further comprising
a biopsy element configured to engage with the MBI system when the first detector head is disengaged from the MBI system,
wherein the biopsy element is configured to receive and pass the biopsy needle therethrough, toward the second detector head, to a target depth defined by the depth of said identified portion of the breast determined based on said radius, and
wherein changes in said image-trace represent removal of a part of the portion of the breast with biopsy.

* * * * *